(12) United States Patent
Watanabe et al.

(10) Patent No.: US 10,246,404 B2
(45) Date of Patent: Apr. 2, 2019

(54) BIFUNCTIONAL COMPOUND HAVING NORBORNANE SKELETON AND PRODUCTION METHOD THEREFOR

(71) Applicant: Mitsubishi Gas Chemical Company, Inc., Chiyoda-ku (JP)

(72) Inventors: Taku Watanabe, Niigata (JP); Takashi Motoi, Kurashiki (JP); Yasuaki Yoshimura, Hiratsuka (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 27 days.

(21) Appl. No.: 15/560,713

(22) PCT Filed: Mar. 25, 2016

(86) PCT No.: PCT/JP2016/059547
§ 371 (c)(1),
(2) Date: Sep. 22, 2017

(87) PCT Pub. No.: WO2016/153018
PCT Pub. Date: Sep. 29, 2016

(65) Prior Publication Data
US 2018/0050978 A1 Feb. 22, 2018

(30) Foreign Application Priority Data
Mar. 25, 2015 (JP) .................... 2015-062203

(51) Int. Cl.
*C07C 67/31* (2006.01)
*C08G 63/06* (2006.01)
(Continued)

(52) U.S. Cl.
CPC ............ *C07C 69/757* (2013.01); *C07C 67/31* (2013.01); *C07C 67/313* (2013.01); *C08G 63/06* (2013.01)

(58) Field of Classification Search
None
See application file for complete search history.

(56) References Cited

U.S. PATENT DOCUMENTS

2017/0088504 A1* 3/2017 Motoi .................... C07C 45/50

FOREIGN PATENT DOCUMENTS

| GB | 1170226 | 11/1969 |
|----|---------|---------|
| JP | 3-200830 A | 9/1991 |

(Continued)

OTHER PUBLICATIONS

(Acetylacetonato)dicarbonylrhodium(I) (Sigma Aldrich product webpage for (Acetylacetonato)dicarbonylrhodium(I), downloaded from https://www.sigmaaldrich.com/catalog/product/aldrich/288101?lang=en&region=US on Mar. 14, 2018).*

(Continued)

*Primary Examiner* — Amy C Bonaparte
(74) *Attorney, Agent, or Firm* — Oblon, McClelland, Maier & Neustadt, L.L.P.

(57) ABSTRACT

The bifunctional compound according to the present invention is represented by the following formula (1):

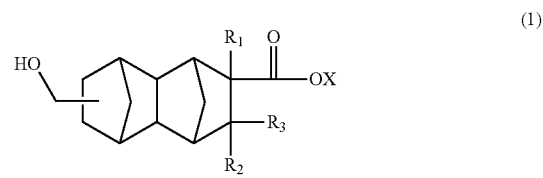

wherein $R_1$ is a hydrogen atom, $CH_3$, or $C_2H_5$; $R_2$ and $R_3$ are each independently a hydrogen atom or $CH_3$; and X is a (Continued)

hydrogen atom or a hydrocarbon group having no more than 4 carbon atoms and optionally containing a hydroxyl group.

5 Claims, 3 Drawing Sheets

(51) Int. Cl.
    *C07C 67/313*     (2006.01)
    *C07C 69/757*     (2006.01)

(56) References Cited

FOREIGN PATENT DOCUMENTS

| | | |
|---|---|---|
| JP | 5-97769 A | 4/1993 |
| JP | 5-125329 A | 5/1993 |
| JP | 2001-10999 A | 1/2001 |
| JP | 2007-161917 A | 6/2007 |
| JP | 2008-233877 A | 10/2008 |
| WO | 2012/035874 A1 | 3/2012 |
| WO | 2012/035875 A1 | 3/2012 |
| WO | 2015/147242 A1 | 10/2015 |

OTHER PUBLICATIONS

International Search Report dated Jun. 14, 2016, in PCT/JP2016/059547, filed Mar. 25, 2016.

\* cited by examiner

BIFUNCTIONAL COMPOUND HAVING NORBORNANE SKELETON AND PRODUCTION METHOD THEREFOR

TECHNICAL FIELD

The present invention relates to a bifunctional compound and a production method therefor and, in particular, a bifunctional compound having a norbornane skeleton within the molecule and a production method therefor.

BACKGROUND ART

Bifunctional compounds having a norbornane skeleton are known to show excellent characteristics when used as adhesives and resin raw materials. Tricyclodecanedimethanol and pentacyclopentadecanedimethanol are known as bifunctional compounds having a norbornane skeleton, and some production methods are reported (see, for example, Patent Document 1).

Patent Document 2 discloses a method for producing tricyclodecanedimethanol by subjecting dicyclopentadiene to a hydroformylation reaction to form dialdehyde and hydrogenating the dialdehyde.

Patent Document 3 discloses a method for producing tricyclodecanedimethanol or pentacyclopentadecanedimethanol by hydroformylating dicyclopentadiene or tricyclopentadiene using a rhodium compound as a catalyst, adding an extraction solvent composed of a polyalcohol to the resulting reaction solution to separate the rhodium complex catalyst into the hydrocarbon-based reaction solvent layer and the reaction-product tricyclodecanedicarbaldehyde or pentacyclopentadecanedicarbaldehyde into the extraction solvent layer, and subjecting the extraction solvent layer to hydrogen reduction in the presence of a hydrogenation catalyst.

Tricyclodecanedimethanol described in Patent Documents 2 and 3 is a compound in which one norbornane and cyclopentane mutually share a plurality of atoms to form the main skeleton as shown in the following formula (A). Pentacyclopentadecanedimethanol described in Patent Document 3 is a compound in which two norbornanes and cyclopentane mutually share a plurality of atoms to form the main skeleton as shown in formula (B) or formula (C).

(A)

(B)

(C)

LIST OF PRIOR ART DOCUMENTS

Patent Document

Patent Document 1: Japanese Patent Laid-Open No. 5-125329

Patent Document 2: UK Patent No. 1170226

Patent Document 3: Japanese Patent Laid-Open No. 2001-10999

SUMMARY OF INVENTION

Problems to be Solved by Invention

Applications of bifunctional compounds are paint additives, adhesives, resin raw materials, and the like. It is generally known that the properties of paints, adhesives, resins, and the like can be modified by using bifunctional compounds having different molecular structures in these applications. Accordingly, a novel bifunctional compound is desired from the viewpoint of modification, property improvement, function provision, and the like. That is, one of the objects of the present invention is to provide a novel bifunctional compound having a norbornane skeleton within the molecule and having a skeleton different from tricyclodecanedimethanol and pentacyclo pentadecanedimethanol.

The method for producing tricyclodecanedimethanol described in Patent Document 2 requires a high-pressure condition of about 20 to 25 MPa. A highly pressure resistant facility is required to industrially perform the method, and therefore the method can hardly be regarded as an economically advantageous method. Moreover, according to the method for producing tricyclodecanedimethanol or pentacyclopentadecanedimethanol described in Patent Document 3, the hydrocarbon-based reaction solvent layer containing a rhodium complex catalyst needs to be recycled in order to reduce the cost of the rhodium complex catalyst, a facility is needed therefor, and thus this method also can hardly be regarded as an economical method. From such viewpoints, an object of the present invention is also to provide a production method that can be industrially performed and is highly economical, in addition to providing a novel bifunctional compound having norbornane within the molecule.

Means for Solving Problems

As a result of having conducted diligent research to solve the above problems, the inventors found that the above problems can be solved by the following invention.

That is, the present invention is as follows.

[1]

A bifunctional compound represented by the following formula (1):

wherein $R_1$ is a hydrogen atom, $CH_3$, or $C_2H_5$; $R_2$ and $R_3$ are each independently a hydrogen atom or $CH_3$; and X is a hydrogen atom or a hydrocarbon group having no more than 4 carbon atoms and optionally containing a hydroxyl group.

[2]

A method for producing a bifunctional compound represented by the following formula (1), the method comprising a step of reducing a bifunctional compound represented by the following formula (2) in the presence of a catalyst having hydrogenation capability and hydrogen:

wherein $R_1$ is a hydrogen atom, $CH_3$, or $C_2H_5$; $R_2$ and $R_3$ are each independently a hydrogen atom or $CH_3$; and X is a hydrogen atom or a hydrocarbon group having no more than 4 carbon atoms and optionally containing a hydroxyl group.

[3]

The method for producing the bifunctional compound according to [2], wherein the catalyst having hydrogenation capability comprises at least one element selected from the group consisting of copper, chromium, iron, zinc, aluminum, nickel, cobalt, and palladium.

[4]

The method for producing the bifunctional compound according to [2] or [3], further comprising a step of subjecting a monoolefin represented by the following formula (3) to a hydroformylation reaction with carbon monoxide and hydrogen gas in the presence of a rhodium compound and an organopshosphorus compound to obtain the bifunctional represented by the above formula (2):

wherein $R_1$, $R_2$, $R_3$, and X are as defined in the above formulae (1) and (2).

[5]

The method for producing the bifunctional compound according to [4], wherein in the hydroformylation reaction, 0.1 to 60 micromoles of the rhodium compound is used per mol of the monoolefin, and the organophosphorous compound is used in an amount of 300 to 10000 mol per mol of rhodium atoms in the rhodium compound.

Advantages of Invention

According to the present invention, a novel bifunctional compound having a norbornane skeleton within the molecule can be obtained by a method that can be industrially performed and is highly economical.

MODE FOR CARRYING OUT INVENTION

Below, an embodiment for carrying out the present invention (hereinafter simply referred to as "the present embodiment") will now be described in detail. The following present embodiment is an example for describing the present invention and is not intended to limit the present invention to the following contents. The present invention can be carried out after suitably making modifications within the scope of the present invention.

The bifunctional compound of the present embodiment is a compound represented by the following formula (1):

In formula (1), $R_1$ is a hydrogen atom, $CH_3$, or $C_2H_5$; $R_2$ and $R_3$ are each independently a hydrogen atom or $CH_3$; and X is a hydrogen atom or a hydrocarbon group having no more than 4 carbon atoms and optionally containing a hydroxyl group. In formula (1), $R_1$ is preferably a hydrogen atom or $CH_3$. $R_2$ and $R_3$ are preferably hydrogen atoms. Here, examples of the hydrocarbon group in the present embodiment include, but are not limited to, a methyl group, an ethyl group, a propyl group, a butyl group, a vinyl group, a 2-hydroxyethyl group, and a 4-hydroxybutyl group.

The bifunctional compound having a norbornane skeleton represented by the above formula (1) demonstrates particularly excellent performance when used as a paint additive, an adhesive, a resin raw material, and the like.

The bifunctional compound represented by formula (1) of the present embodiment can be synthesized through, for example, the route shown in equation (I) using dicyclopentadiene or cyclopentadiene and an olefin having a functional group as raw materials:

wherein $R_1$, $R_2$, $R_3$, and X are as defined in the above formulae (1) and (2).

[Production of Monoolefin Having 13 to 21 Carbon Atoms Represented by Formula (3)]

The monoolefin having 13 to 21 carbon atoms represented by formula (3) in the present embodiment can be produced by, for example, carrying out a Diels Alder reaction of an olefin having a functional group with dicyclopentadiene.

In formula (3), $R_1$, $R_2$, $R_3$, and X are as defined in the above formulae (1) and (2).

Specific examples of the olefin having a functional group used in the Diels Alder reaction include, but are not limited to, methacrylic acid, methyl methacrylate, ethyl methacrylate, propyl methacrylate, butyl methacrylate, vinyl methacrylate, 2-hydroxyethyl methacrylate, 4-hydroxybutyl methacrylate, acrylic acid, methyl acrylate, ethyl acrylate, propyl acrylate, butyl acrylate, vinyl acrylate, 2-hydroxyethyl acrylate, 4-hydroxybutyl acrylate, crotonic acid, methyl crotonate, ethyl crotonate, 3-methylcrotonic acid, methyl 3-methylcrotonate, and ethyl 3-methylcrotonate. Preferable olefins are methacrylic acid, methyl methacrylate, 2-hydroxyethyl methacrylate, acrylic acid, methyl acrylate, and 2-hydroxyethyl acrylate, and more preferable olefins are methyl methacrylate and methyl acrylate.

Moreover, examples of the olefin having a functional group used in the Diels Alder reaction also include acrylonitrile, methacrylonitrile, acrolein, and methacrolein. When these olefins are used as raw materials, the monoolefin represented by general formula (4') can fee produced via, for example, the routes shown in the following equation (II) and equation (III).

wherein $R_1$ is a hydrogen atom or $CH_3$.

Dicyclopentadiene used for the Diels Alder reaction in the present embodiment preferably has a high purity, and the content of butadiene, isoprene, and the like is preferably reduced. The purity of dicyclopentadiene is preferably 90% or higher, and more preferably 95% or higher. Dicyclopentadiene tends to depolymerize under heating conditions and become cyclopentadiene (so-called monocyclopentadiene), and therefore it is also possible to use cyclopentadiene in place of dicyclopentadiene. It is considered that the monoolefin having 13 to 21 carbon atoms represented by formula (3) is substantially produced via a monoolefin having 8 to 16 carbon atoms represented by the following formula (7) (a product of a first-stage Diels Alder reaction), and it is considered that the produced monoolefin of formula (7) undergoes a Diels Alder reaction (a second-stage Diels Alder reaction) with cyclopentadiene (Diene) present in the reaction system as a new parent diene compound (Dienophile) to produce the monoolefin having 13 to 21 carbon atoms represented by formula (3):

(7)

wherein $R_1$, $R_2$, $R_3$, and X are as defined in the above formulae (1) and (2).

In order to allow the second-stage Diels Alder reaction to efficiently proceed, it is important that cyclopentadiene be present in the reaction system, and therefore the reaction temperature is preferably 100° C. or higher, more preferably 120° C. or higher, and even more preferably 130° C. or higher. On the other hand, in order to suppress the generation of high-boiling substances, it is preferable to carry out the reaction at a temperature of 250° C. or lower. It is also possible to use hydrocarbons, alcohols, esters, and the like as reaction solvents, and aliphatic hydrocarbons having 6 or more carbon atoms, cyclohexane, toluene, xylene, ethylbenzene, mesitylene, propanol, butanol, and the like are preferable. A known catalyst such as $AlCl_3$ may be added as necessary.

As a reaction mode of the Diels Alder reaction of the present embodiment, various reaction modes can be adopted, such as a batch mode by a tank reactor or the like, a semi-batch mode where a substrate or a substrate solution is supplied to a tank reactor under reaction conditions, and a continuous flow mode where a substrate or the like is allowed to flow through a tubular reactor under reaction conditions.

The reaction product obtained in the Diels Alder reaction of the present embodiment can also be used as-is as a raw material for the next hydroformylation reaction, and it may also be subjected to the next step after purification by distillation, extraction, crystallization, or a like method.

[Production of Bifunctional Compound Having 14 to 22 Carbon Atoms Represented by Formula (2)]

The bifunctional compound having 14 to 22 carbon atoms represented by formula (2) in the above equation (I) of the present embodiment can be produced by, for example, subjecting the monoolefin having 13 to 21 carbon atoms represented by formula (3), carbon monoxide, and hydrogen gas to a hydroformylation reaction in the presence of a rhodium compound and an organophosphorus compound.

The rhodium compound used in the hydroformylation reaction of the present embodiment may be a compound that forms a complex with an organophosphorus compound and shows hydroformylating activity in the presence of carbon monoxide and hydrogen, and the form of the precursor thereof is not particularly limited. For example, a catalyst precursor substance such as rhodium acetylacetonatodicarbonyl (hereinafter referred to as $Rh(acac)(CO)_2$), $Rh_2O_3$, $Rh_4(CO)_{12}$, $Rh_6(CO)_{16}$, or $Rh(NO_3)_3$ may be introduced into a reaction mixture together with an organophosphorus compound to form a rhodium metal hydride carbonyl phosphorus complex having catalytic activity in a reaction vessel, or a rhodium metal hydride carbonyl phosphorus complex may be prepared in advance and introduced into a reactor. A preferable specific example in the present embodiment is a method in which $Rh(acac)(CO)_2$ is reacted with an organophosphorous compound in the presence of a solvent and then introduced into a reactor together with an excess of the organophosphorus compound to form a rhodium-organophosphorus complex having catalytic activity.

What was surprising to the present inventors was that the product of the two-stage Diels Alder reaction containing an internal olefin having a relatively large molecular weight as represented by formula (3) was hydroformylated with an extremely small amount of a rhodium catalyst. The amount of the rhodium compound used in the hydroformylation reaction in the present embodiment is preferably 0.1 to 60 micromoles, more preferably 0.1 to 30 micromoles, even more preferably 0.2 to 20 micromoles, and particularly preferably 0.5 to 10 micromoles per mol of the monoolefin having 13 to 21 carbon atoms represented by formula (3), which is the substrate of the hydroformylation reaction. An amount of the rhodium compound used of less than 60 micromoles per mol of the monoolefin having 13 to 21 carbon atoms can be evaluated as being at a level where practically a recovery/recycle facility for the rhodium complex does not need to be provided. Thus, according to the present embodiment, the economic burden concerning a recovery/recycle facility can be reduced, and the cost of the rhodium catalyst can be sufficiently reduced.

In the hydroformylation reaction in the present embodiment, the organophosphorus compound that forms a catalyst for the hydroformylation reaction together with the rhodium compound is not particularly limited, and examples include phosphines represented by general formula $P(-R_a)(-R_b)(-R_c)$ or phosphites represented by $P(-OR_a)(-OR_b)(-OR_c)$. Specific examples of $R_a$, $R_b$, and $R_c$ include, but are not limited to, aryl groups that may be substituted with an alkyl group or an alkoxy group having 1 to 4 carbon atoms and alicyclic alkyl groups that may be substituted with an alkyl group or an alkoxy group having 1 to 4 carbon atoms, and triphenylphosphine and triphenylphosphite are suitably used. The amount of the organophosphorus compound used is preferably 300 mol to 10000 mol, more preferably 500 mol to 10000 mol, even more preferably 700 mol to 5000 mol, and particularly preferably 900 mol to 2000 mol per mol of the rhodium atoms in the rhodium compound. When the amount of the organophosphorous compound used is 300 mol or more per mol of the rhodium atoms, there is a tendency that the stability of the rhodium metal hydride carbonyl phosphorus complex, which is the catalyst active material, can be sufficiently ensured, and, as a result, good reactivity tends to be ensured. An amount of the organophosphorus compound used of 10000 mol or less per mol of the rhodium atoms is preferable from the viewpoint of sufficiently reducing the cost of the organophosphorus compound.

Although the hydroformylation reaction in the present embodiment can also be carried out without using a solvent, the use of a solvent that is inert to the reaction makes it possible to more suitably carry out the reaction. The solvent usable in the hydroformylation reaction is not particularly limited as long as it dissolves monoolefin having 13 to 21 carbon atoms represented by formula (3), dicyclopentadiene or cyclopentadiene, the above rhodium compound, and the above organophosphorus compound. Specific examples include, but are not limited to, hydrocarbons such as aliphatic hydrocarbons, alicyclic hydrocarbons, and aromatic hydrocarbons; esters such as aliphatic esters, alicyclic esters, and aromatic esters; alcohols such as aliphatic alcohols and alicyclic alcohols; and aromatic halides and such solvents.

Among these, hydrocarbons are suitably used, and, in particular, alicyclic hydrocarbons and aromatic hydrocarbons are more suitably used.

The temperature when carrying out the hydroformylation reaction in the present embodiment is preferably 40° C. to 160° C., and more preferably 80° C. to 140° C. When the reaction temperature is 40° C. or higher, a sufficient reaction rate tends to be obtained, and remainders of the raw-material monoolefin tend to be more suppressed. When the reaction temperature is 160° C. or lower, there is a tendency that the generation of byproducts derived from the raw-material monoolefin and the reaction product is suppressed, and deterioration of reaction results can be effectively prevented.

When the hydroformylation reaction in the present embodiment is carried out, the reaction is preferably carried out under an increased pressure of carbon monoxide (hereinafter also referred to as "CO") and hydrogen (hereinafter also referred to as "$H_2$") gas. At that time, CO and $H_2$ gas can be each independently introduced into the reaction system and, also, can be introduced into the reaction system as a mixed gas prepared in advance. The molar ratio (=CO/$H_2$) of CO and $H_2$ gas introduced into the reaction system is preferably 0.2 to 5, more preferably 0.5 to 2, and even more preferably 0.8 to 1.2. When the molar ratio of CO and $H_2$ gas is adjusted to the above range, the reaction activity of the hydroformylation reaction and selectivity for the intended aldehyde tend to be good. CO and $H_2$ gas introduced into the reaction system decreases as the reaction progresses, and therefore the reaction may be easily controlled by the use of a mixed gas of CO and $H_2$ prepared in advance.

The reaction pressure of the hydroformylation reaction in the present embodiment is preferably 1 to 12 MPa, more preferably 1.5 to 8 MPa, and even more preferably 1.5 to 5 MPa. With the reaction pressure being 1 MPa or higher, a sufficient reaction rate tends be obtained, and there is a tendency that remainders of the raw-material monoolefin can be sufficiently suppressed. A reaction pressure of 12 MPa or lower makes an expensive facility having excellent pressure resistance unnecessary and is therefore economically advantageous. In particular, when the reaction is carried out in a batch or semi-batch mode, CO and $H_2$ gas need to be discharged or pressure-released after the end of the reaction, and a lower pressure results in a smaller loss of CO and $H_2$ gas and is therefore economically advantageous.

As a reaction mode when carrying out the hydroformylation reaction in the present embodiment, a batch reaction and a semi-batch reaction are suitable. A semi-batch reaction can be carried out by adding a rhodium compound, an organophosphorus compound, and the above solvent to a reactor, setting the described reaction conditions by increasing the pressure by CO/$H_2$ gas, raising the temperature, or the like, and then supplying the raw-material monoolefin or a solution thereof to the reactor.

The reaction product obtained in the hydroformylation reaction can also be used as-is as a raw material for the next reduction reaction, and it may also be subjected to the next step after purification by, for example, distillation, extraction, or crystallization.

[Production of Bifunctional Compound Having 14 to 22 Carbon Atoms Represented by Formula (1)]

The bifunctional compound having 14 to 22 carbon atoms represented by formula (1) in the above equation (I) of the present embodiment can be produced by reducing the bifunctional compound having 14 to 22 carbon atoms represented by formula (2) in the presence of a catalyst having hydrogenation capability and hydrogen.

In the reduction reaction in the present embodiment, it is preferable to use a catalyst containing at least one element selected from the group consisting of copper, chromium, iron, zinc, aluminum, nickel, cobalt, and palladium as the catalyst having hydrogenation capability. More preferable catalysts are a Cu—Cr catalyst, a Cu—Zn catalyst, a Cu—Zn—Al catalyst, a Raney-Ni catalyst, a Raney-Co catalyst, and the like. Even more preferable catalysts are a Cu—Cr catalyst and a Raney-Co catalyst.

The amount of the hydrogenation catalyst used is preferably 1 to 100 mass %, more preferably 2 to 50 mass %, and even more preferably 5 to 30 mass % relative to the substrate bifunctional compound having 14 to 22 carbon atoms represented by formula (2). With the amount of the catalyst used being within these ranges, the hydrogenation reaction can be suitably carried out. When the amount of the catalyst used is 1 mass % or more, the reaction sufficiently progresses, and, as a result, there is a tendency that a sufficient yield of the intended product can be ensured. When the amount of the catalyst used is 100 mass % or less, the balance between the amount of the catalyst subjected to the reaction and the effect of improving the reaction rate tends to be good.

The reaction temperature of the reduction reaction in the present embodiment is preferably 60 to 200° C., and more preferably 80 to 150° C. With the reaction temperature being 200° C. or lower, side reactions and degradation reactions are suppressed, and the intended product tends to be obtained in high yield. With the reaction temperature being 60° C. or higher, the reaction can be completed in an appropriate time, and there is a tendency that a decrease in productivity and a decrease in the yield of the intended product can be avoided.

The reaction pressure of the reduction reaction in the present embodiment is preferably 0.5 to 10 MPa and more preferably 1 to 5 MPa as hydrogen partial pressure. With the hydrogen partial pressure being 10 MPa or lower, side reactions and degradation reactions are suppressed, and the intended product tends to be obtained in high yield. With the hydrogen partial pressure being 0.5 MPa or higher, the reaction can be completed in an appropriate time, and there is a tendency that a decrease in productivity and a decrease in the yield of the intended product can be avoided. It is also possible to allow a gas that is inert to the reduction reaction (such as nitrogen or argon) to be concomitantly present.

In the reduction reaction in the present embodiment, a solvent can be used. Examples of the solvent used in the reduction reaction include aliphatic hydrocarbons, alicyclic hydrocarbons, aromatic hydrocarbons, and alcohols, and, in particular, alicyclic hydrocarbons, aromatic hydrocarbons, and alcohols are suitable. Specific examples include cyclohexane, toluene, xylene, methanol, ethanol, and 1-propanol.

As a reaction mode of the reduction reaction in the present embodiment, various reaction modes can be adopted, such as a batch mode by a tank reactor or the like, a semi-batch mode where a substrate or a substrate solution is supplied to a tank reactor under reaction conditions, and a continuous-flow mode where a substrate or a substrate solution is allowed to flow through a tubular reactor filled with a shaped catalyst under reaction conditions.

The reaction product obtained in the reduction reaction in the present embodiment can be purified by, for example, distillation, extraction, or crystallization.

EXAMPLES

Below, the present embodiment will now be described in more detail by way of Examples, but the present embodiment is not limited to these Examples.

11

<Analytical Methods>
1) Gas Chromatography Measurement Conditions
   Analyzer: Capillary Gas Chromatograph GC-2010 Plus manufactured by Shimadzu Corporation
   Analytical column: InertCap 1 manufactured by GL Sciences Inc. (30 m, 0.32 mm I.D., film, thickness 0.25 μm
   Oven temperature: 60° C. (for 0.5 min)-15° C./min-280° C. (for 4 min)
   Detector: FID, temperature 280° C.
2) GC-MS Measurement Conditions
   Analyzer: GCMS-QP2010 Plus manufactured by Shimadzu Corporation
   Ionization voltage: 70 eV
   Analytical column: DB-1 manufactured by Agilent Technologies (30 m, 0.32 mm I.D., film thickness 1.00 μm)
   Oven temperature: 60° C. (for 0.5 min)-15° C./min-280° C. (for 4 min)
3) HMR Measurement Conditions
   Apparatus: JNM-ECA500 (500 MHz) manufactured by JEOL Ltd.
   Measurement mode: 1H-NMR, 13C-NMR, COSY-NMR
   Solvent: $CDCl_3$ (heavy chloroform)
   Internal standard: tetramethylsilane

Example 1

173 g (2.01 mol) of methyl acrylate and 167 g (1.26 mol) of dicyclopentadiene were charged into a 500 mL stainless-steel reactor and reacted at 195° C. for 2 hours. From the reaction, a reaction solution containing 96 g of monoolefin represented by the following formula (3a) was obtained, this was purified by distillation, and then some was subjected to the following reaction.

Using a 300 mL stainless-steel reactor, the hydroformylation reaction of the monoolefin represented by formula (3a) that had been purified by distillation was carried out with $CO/H_2$ mixed gas ($CO/H_2$ molar ratio=1). To the reactor were added 70 g of the monoolefin represented by formula (3a), 140 g of toluene, 0.50 g of triphenylphosphite, 550 μL of a separately prepared toluene solution of Rh(acac)(CO)$_2$ (concentration 0.003 mol/L). Replacement by nitrogen and $CO/H_2$ mixed gas was each performed 3 times, then the pressure inside the system was increased by $CO/H_2$ mixed gas, and a reaction was carried out at 100° C. at 2 MPa for 5 hours. After the end of the reaction, a gas chromatography analysis of the reaction solution verified that the reaction solution (degree of conversion 98%, selectivity 97%) contained 76 g a bifunctional compound represented by formula (2a) and 1.4 g of monoolefin represented by formula (3a), also, this was purified by distillation, and some was subjected to the following reaction.

To a 300 mL stainless-steel reactor were added 54 g of the bifunctional compound represented by formula (2a) that had been purified by distillation, 7 mL of a sponge cobalt catalyst (manufactured by Nikko Rica Corporation: R-400), and 109 g of toluene, the system was pressurized by hydrogen gas, and a reaction was carried out at 3 MPa at 100° C. for 9 hours. After the reaction, the resulting slurry was filtered through a membrane filter having a pore size of 0.2 μm to remove the catalyst. Thereafter, an evaporator was used to distill off the solvent, and gas chromatography and GC-MS analyses verified that 51 g of a main product having a molecular weight of 250 was contained (main-product yield 93%). This was further purified by distillation, and the main product was obtained.

(3a)

(2a)

(1a)

wherein Me represents a methyl group.

<Identification of Product>

The components obtained in Example 1 were analyzed by NMR. NMR spectra are shown in FIGS. 1 to 3.

Figure 1:
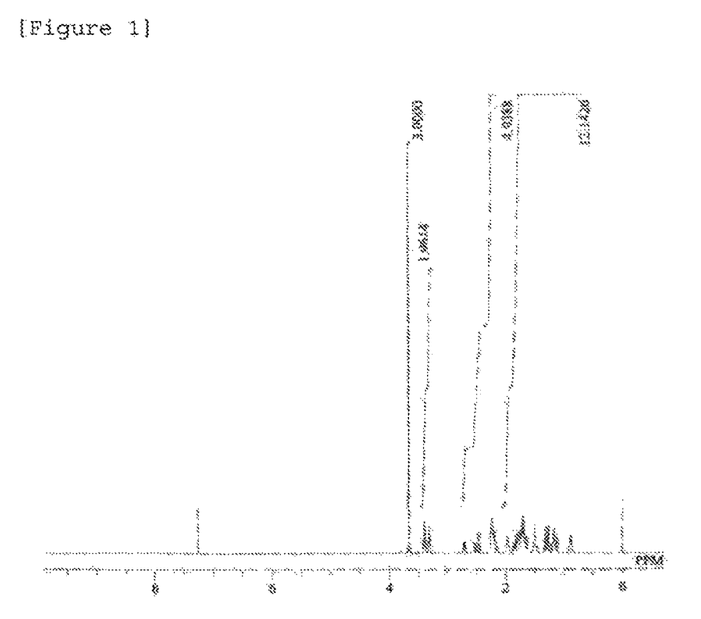
FIG. 1 shows the results of 1H-NMR measurement of the main reaction product obtained in Example 1.
Figure 2:
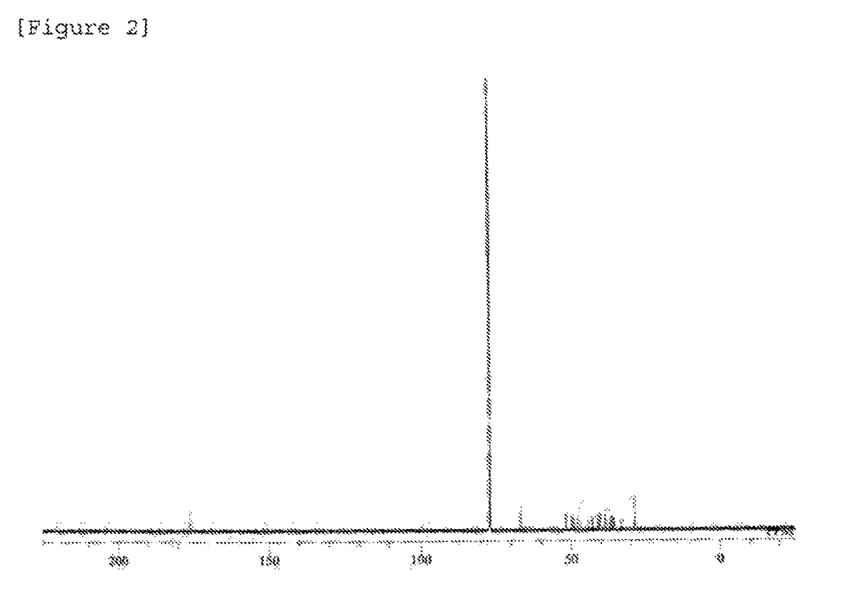
FIG. 2 shows the results of 13C-NMR measurement of the main reaction product obtained in Example 1.
Figure 3:
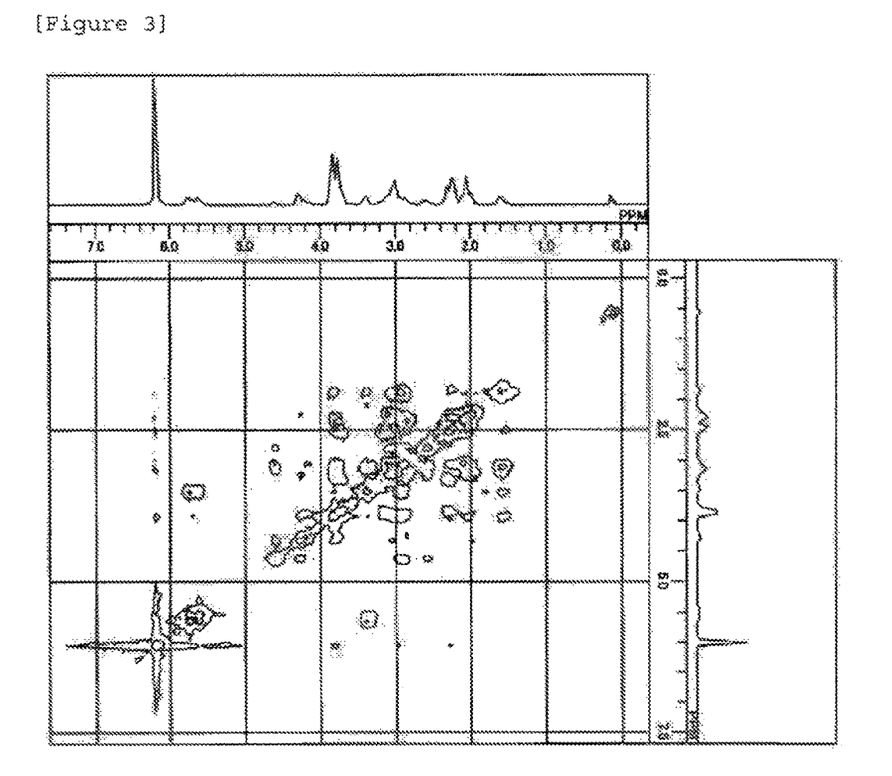
FIG. 3 shows the results of COSY-NMR measurement of the main reaction product obtained in Example 1.

From the results of a GC-MS analysis, and NMR analyses of FIGS. 1 to 3, the main product obtained in Example 1 was verified as a bifunctional compound represented by the above formula (1a).

The bifunctional compound obtained above was used to produce a polyester resin as follows, and the physical properties thereof were evaluated in the following manner.

(1) Weight Average Molecular Weight (Mw)

The polyester resin was dissolved in tetrahydrofuran to have a polyester resin concentration of 0.2 mass % and measured by gel permeation chromatography (GPC) to determine the molecular weight in reference to standard polystyrene. A column TSKgel SuperHM-M manufactured by Tosoh Corporation was used for GPC measurement at a column temperature of 40° C. The eluent tetrahydrofuran was allowed to flow at a flow rate of 0.6 mL/min for measurement by an RI detector.

(2) Glass Transition Temperature (Tg)

The glass transition temperature of the polyester resin was measured as follows. Using a differential scanning calorimeter (manufactured by Shimadzu Corporation, trade name: DSC/TA-60WS), about 10 mg of the polyester resin was placed in an unsealed aluminum container and heated to 280° C. at a heating rate of 20° C./min in a nitrogen gas stream (30 mL/min), and the dissolved polyester resin was rapidly cooled to give a measurement sample. The sample was measured under the same conditions, and the temperature which changes by only ½ of the difference in the baseline between the DSC curve before and that after transition was regarded as the glass transition temperature.

(3) Transparency

A sample was formed by pressing the polyester resin into a disk (thickness 3 mm) to measure the total light transmission rate. A color-difference/turbidity meter (manufactured by Nippon Denshoku Industries Co., Ltd., trade name: COH-400) was used for measurement.

(4) Water Vapor Transmission Coefficient (g·Mm/m$^2$·Day)

A water vapor transmission rate testing system (manufactured by MOCON Inc., trade name: PERMATRAN-W Model 1/50G) was used to measure the water vapor transmission rate of a coated substrate under conditions having 40° C. and a relative humidity of 90%, and the water vapor transmission coefficient of the coating film was calculated using the following equation:

$$1/R_1 = 1/R_2 + DFT/P$$

where
$R_1$=Water vapor transmission rate of coated substrate (g/m²·day)
$R_2$=Water vapor transmission rate of substrate (g/m²·day)
DFT=Thickness of coating film (mm)
P=Water vapor transmission coefficient of coating film (g·mm/m²·day)

Example 2

45 g of the compound represented by formula (1a) obtained in Example 1 and 0.007 g of tetrabutyl titanate were charged into a 200 mL polyester production apparatus equipped with a partial condenser, a total condenser, a cold trap, a stirrer, a heater, and a nitrogen inlet tube, heated to 230° C. in a nitrogen atmosphere, and then retained for 1 hour. Thereafter, heating and depressurization were gradually carried out, and eventually polycondensation was carried out at 270° C. at 0.1 kPa or lower. The reaction was terminated when an appropriate melt viscosity was reached, and a polyester resin was thus obtained. The resulting polyester resin had a weight average molecular weight of 26000, a glass transition temperature of 167° C., and a total light transmission rate of 91%.

Example 3

11.5 g of the compound represented by formula (1a) obtained in a monomer synthesis example and 0.005 g of tetrabutyl titanate were charged into a 30 mL polyester production apparatus equipped with a partial condenser, a total condenser, a cold trap, a stirrer, a heater, and a nitrogen inlet tube, heated to 230° C. in a nitrogen atmosphere, and then retained for 1 hour. Thereafter, heating and depressurization were gradually carried out, and eventually polycondensation was carried out at 270° C. at 0.1 kPa or lower. The reaction was terminated when an appropriate melt viscosity was reached, and a polyester resin was thus obtained. The resulting polyester resin had a weight average molecular weight of 46800, a glass transition temperature of 171° C., and a total light transmission rate of 91%.

Then, 20 parts by mass of the resulting polyester resin and 80 parts by mass of tetrahydrofuran were mixed to obtain an application liquid having a solid content concentration of 20 wt %. A stretched polyethylene terephthalate film (Ester Film E5100 manufactured by Toyobo Co., Ltd.) having a thickness of 50 μm was used as a substrate, a bar coater No. 20 was used to apply the application liquid to the substrate, and the application liquid was dried at 100° C. for 60 minutes to obtain a coat film. The water vapor transmission rate of the resulting coat film was evaluated. The thickness of the coat layer was 5.7 μm, and the water vapor transmission coefficient calculated from the water vapor transmission rate was 1.14 g·mm/m²·day (40° C. 90% RH).

Comparative Monomer Synthesis Example

95 g (1.10 mol) of methyl acrylate and 105 g (0.79 mol) of dicyclopentadiene were charged into a 500 mL stainless-steel reactor and reacted at 195° C. for 2 hours. A reaction solution containing 127 g of monoolefin represented by the following formula (8) and 55 g of monoolefin represented by formula (3a) was obtained. This was purified by distillation to thereby obtain monoolefin represented by formula (8), and some was subjected to the following reaction.

Using a 500 mL stainless-steel reactor, the hydroformylation reaction of the monoolefin represented by formula (8) that had been purified by distillation was carried out with CO/H₂ mixed gas (CO/H₂ molar ratio=1). To the reactor were added 100 g of the monoolefin represented by formula (8), 200 g of toluene, 0.614 g of triphenylphosphite, 200 μL of a separately prepared toluene solution of Rh(acac)(CO)₂ (concentration 0.0097 mol/L). Replacement by nitrogen and CO/H₂ mixed gas was each performed 3 times, then the pressure inside the system was increased by CO/H₂ mixed gas, and a reaction was carried out at 100° C. at 2 MPa for 4.5 hours. After the end of the reaction, a gas chromatography analysis of the reaction solution verified that the reaction solution (degree of conversion 100%, selectivity 94%) contained 113 g a bifunctional compound represented by formula (9), also, this was purified by distillation, and some was subjected to the following reaction.

To a 500 mL stainless-steel reactor were added 70 g of the bifunctional compound represented by formula (9) that had been purified by distillation, 14 mL of a sponge cobalt catalyst (manufactured by Nikko Rica Corporation: R-400), and 210 g of toluene, the system was pressurized by hydrogen gas, and a reaction was carried out at 3 MPa at 100° C. for 3.5 hours. After the reaction, the resulting slurry was filtered through a membrane filter having a pore size of 0.2 μm to filter the catalyst. Thereafter, an evaporator was used to distill off the solvent, and a GC-MS analysis verified that 69 g of a main product having a molecular weight of 184 was contained (main-product yield 98%). This was further purified by distillation, and the main product (10) was obtained.

(8)

(9)

(10)

Comparative Example 1

A reaction was carried out by the same method as in Example 3 to obtain a polyester resin except that the compound represented by formula (10) obtained in the comparative monomer synthesis example was used as a raw-material monomer, and the final temperature of polycondensation was 265° C. Further, the resulting resin was used to form a coat film by the same procedure as in Example 3, the water vapor transmission rate was measured, and the water vapor transmission coefficient was calculated. The weight average molecular weight, the glass transition temperature, and the water vapor transmission coefficient of the resulting polyester resin are shown in Table 1. The total light transmission rate of the resulting polyester resin was 91%.

TABLE 1

|  |  | Example 3 | Comparative Example 1 | Substrate alone |
|---|---|---|---|---|
| Resin evaluation |  |  |  |  |
| Mw |  | 46800 | 35000 | — |
| Mn |  | 17200 | 12400 | — |
| Tg | °C. | 171 | 90 | — |
| Water vapor transmission rate measurement (conditions: 40° C./90% RH) |  |  |  |  |
| Water vapor transmission rate (substrate + coat layer) | g/m2 · day | 12.9 | 13.4 | 13.8 |
| Coat layer thickness | μm | 5.7 | 6.9 | — |
| Water vapor transmission coefficient of coat layer | g · mm/ m2 · day | 1.1 | 3.2 | — |

The water vapor transmission rate of Example 3 was 12.9 g/m²·day, lower than the water vapor transmission rate of 13.8 g/m²·day attained with a substrate alone. When evaluated in terms of water vapor transmission coefficient, the water vapor transmission coefficient of the resin of Example 3 is about ⅓ of the resin of Comparative Example 1. It can be understood from above that the bifunctional compound of the present embodiment can provide a polyester resin having excellent heat resistance and transparency and, moreover, excellent water vapor barrier properties.

The present application is based on a Japanese Patent Application (Japanese Patent Application No. 2015-062203) filed with Japan Patent Office on Mar. 25, 2015, and the entire contents of which are hereby incorporated by reference.

INDUSTRIAL APPLICABILITY

According to the present invention, a novel bifunctional compound having a norbornane skeleton within the molecule and having a skeleton different from tricyclodecanedicarbaldehyde and pentacyclopentadecanedicarbaldehyde can be industrially obtained by a highly economical method.

The invention claimed is:

1. A bifunctional compound, represented by formula (1):

(1)

wherein
$R_1$ is a hydrogen atom, $CH_3$, or $C_7H_5$;
$R_2$ and $R_3$ are each independently a hydrogen atom or $CH_3$; and
X is a hydrogen atom or a hydrocarbon group comprising no more than 4 carbon atoms and optionally a hydroxyl group.

2. A method for producing a bifunctional compound represented by formula (I), the method comprising
reducing a bifunctional compound represented by formula (2) in the presence of a catalyst having hydrogenation capability and hydrogen:

(1)

(2)

wherein
$R_1$ is a hydrogen atom, $CH_3$, or $C_2H_5$;
$R_2$ and $R_3$ are each independently a hydrogen atom or $CH_3$; and
X is a hydrogen atom or a hydrocarbon group comprising no more than 4 carbon atoms and optionally a hydroxyl group.

3. The method according to claim 2, wherein the catalyst comprises at least one element selected from the group consisting of copper, chromium, iron, zinc, aluminum, nickel, cobalt, and palladium.

4. The method according to claim 2, further comprising
subjecting a monoolefin represented by formula (3) to a hydroformylation reaction with carbon monoxide and hydrogen gas in the presence of a rhodium compound and an organophosphorus compound to obtain the bifunctional compound represented by the above formula (2):

(3)

wherein $R_1$, $R_2$, $R_3$, and X are as defined in the formulae (1) and (2).

5. The method according to claim 4, wherein in the hydroformylation reaction, 0.1 to 60 micromoles of the rhodium compound is used per mol of the monoolefin, and the organophosphorus compound is used in an amount of 300 to 10000 mol per mol of rhodium atoms in the rhodium compound.

* * * * *